United States Patent [19]

Suarez

[11] Patent Number: 5,350,766
[45] Date of Patent: Sep. 27, 1994

[54] METHOD FOR THE PREVENTION AND/OR PALLIATION OF THE COMPLICATIONS OF DIABETES USING N-ALPHA ORGININE ACETYL

[75] Inventor: Gerardo Suarez, New Rochelle, N.Y.

[73] Assignee: New York Medical College, Valhalla, N.Y.

[21] Appl. No.: 993,732

[22] Filed: Dec. 18, 1992

[51] Int. Cl.$^5$ ................ A61K 31/195; A61K 31/21; A61K 31/22
[52] U.S. Cl. .................... 514/561; 514/565; 514/866; 514/551; 514/546
[58] Field of Search ............. 514/561, 562, 565, 866, 514/551, 546

[56] References Cited

U.S. PATENT DOCUMENTS

| | | | |
|---|---|---|---|
| 4,100,160 | 7/1978 | Walser | 424/274 |
| 4,678,620 | 7/1987 | Tomic | 424/127 |
| 5,047,398 | 9/1991 | Ferring | 514/15 |
| 5,077,313 | 12/1991 | Lubec | 514/565 |
| 5,217,997 | 6/1993 | Levere et al. | 514/565 |

OTHER PUBLICATIONS

CA: vol. 116 (21) #207710f–Lubec et al (1992).
Portha et al, The American Journal of Medicine, vol. 90 (Suppl 6A) pp. 6A15S–6A21S (1991).
Nephron 1992: 62:80–83; "L-Arginine Reduces Glomerular Basement Membrane Collagen N-Carboxymethyllysine in the Diabetic db/db Mouse", M. Weninger et al., Vienna, Austria.
Nephron 1990; 56:281–284; "The Effect of Substance L on Glucose-Mediated Cross-Links of Collangen in the Diabetic db/db Mouse", G. Lubec et al., Vienna, Austria.

Primary Examiner—Marianne M. Cintins
Assistant Examiner—T. J. Criares

[57] ABSTRACT

The invention relates to a method for treating the complications of diabetes mellitus which comprises the administration to an individual afflicted with diabetes mellitus of an effective amount of N-alpha acetyl arginine.

4 Claims, 3 Drawing Sheets

METHOD FOR THE PREVENTION AND/OR PALLIATION OF THE COMPLICATIONS OF DIABETES USING N-ALPHA ORGININE ACETYL

BACKGROUND OF THE INVENTION

Diabetics are usually classified as having insulin dependent diabetes mellitus or non-insulin dependent diabetes mellitus. Diabetic patients exhibit hyperglycemia in the early stages of the disease but in later stages exhibit large vessel disease, microvascular disease, neuropathy, nephropathy, cataracts, ketoacidosis and diverse symptoms that are caused by these complications. The general treatment for diabetes is the use of insulin or synthetic oral hypoglycemic agents to control the hyperglycemia which is universally observed in diabetics. Even when blood glucose levels are reduced by insulin or oral hypoglycemic agents, over a period of time the complications of diabetes tend to occur in almost all patients in one form or another.

The present invention is concerned with the new use of a pharmacological agent which when administered to a diabetic will prevent, reverse or act as a palliative for the complications of diabetes mellitus. The pharmacological agents which are useful for this purpose are arginine or an arginine derivative which are administered in effective amounts before the complications of diabetes are observed.

In addition the applicant has discovered that the administration of arginine or an arginine derivative will inhibit the Maillard reaction in vivo. The Maillard reaction is the non-enzymatic glycation of proteins which results in the production of glycated proteins. The literature has many references to studies which have found elevated levels of glycated proteins in diabetes mellitus. The inhibition of the Maillard reaction is desirable because it has been described in the literature as the biochemical pathway that is responsible for the sequelae of long standing diabetes and is associated with aging.

Therefore, it is a primary object of this invention to provide a novel method for the prevention of the complications of diabetes mellitus.

It is also an object of this invention to provide a novel method for the palliation of the complications of diabetes mellitus which will reduce the severity of the complications of diabetes mellitus.

It is also an object of this invention to provide novel method for modifying the effects of aging by administering a pharmacological agent which will inhibit the Maillard reaction in vivo.

These and other objects of the present invention will become apparent from a review of the appended specification.

SUMMARY OF THE INVENTION

The present invention comprises a method for the prevention, reversal or palliation of the complications of diabetes mellitus which comprises the administration to an individual afflicted with diabetes mellitus of a effective amount of a compound of Formula 1:

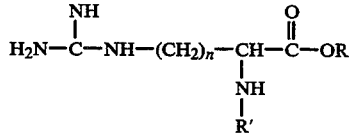

(I)

wherein R is hydrogen, amino or lower alkyl of 1 to 5 carbon atoms; R' is hydrogen or R"CO— where R" is lower alkyl of 1 to 5 carbon atoms and n is the whole integer 1, 2, or 3.

The method comprises the oral or parenteral administration of a compound of Formula 1 to a mammal in a dose which is effective to prevent, reverse or palliate the complications of diabetes mellitus. The term mammal as used herein includes humans as well as animals.

DETAILED DESCRIPTION OF THE INVENTION

Figure 1:
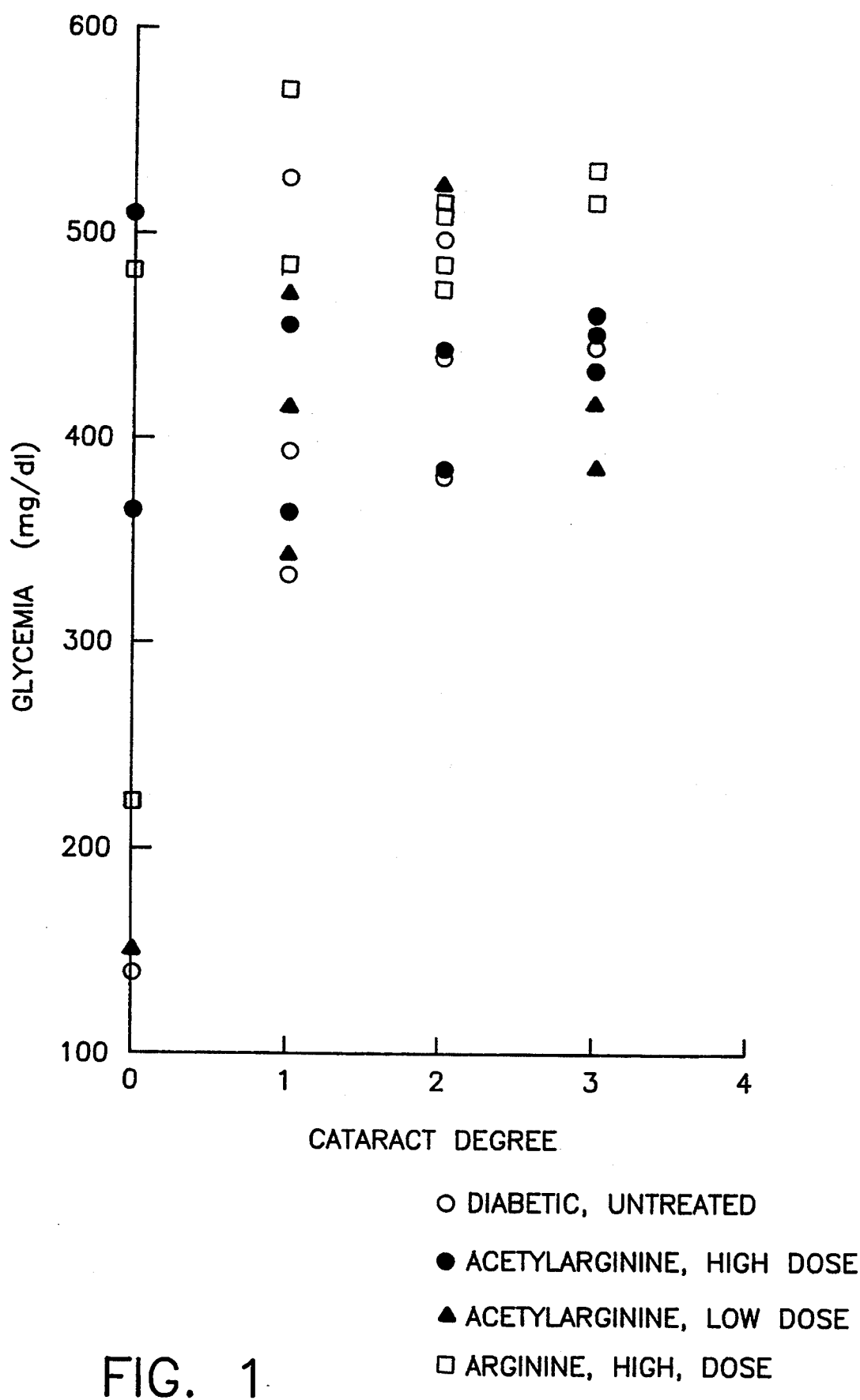
FIG. 1 is a graph which shows the effects of the administration of arginine and N-alpha-acetyl arginine in the prevention of cataracts in diabetic rats.

The oral dosage for the compounds of Formula 1 is from about 10 mg/Kg to about 125 mg/Kg of body weight or more preferably a dose of 12.5 mg/Kg to 100 mg/Kg of body weight administered daily in 2 to 4 divided doses for the prevention or palliation of the complications of diabetes mellitus. The dose for the inhibition of the Maillard reaction is the same as the dose for the prevention or palliation of the complications diabetes mellitus. The parenteral dose for the prevention or palliation of the complications of diabetes mellitus is from 5 mg/Kg to 200 mg/Kg of body weight administered daily in 2 to 4 divided doses.

When the compounds of Formula 1 are administered parenterally, they may be dispersed in water or dissolved in a suitable liquid vehicle. If necessary a preservative may be added to prevent microbial growth.

The injectable compositions may be prepared in the form of unit dose packaged, sterile aqueous solutions or dispersions and sterile powders for the extemporaneous preparation of sterile injectable solutions or dispersions. The carrier can be a solvent or dispersion medium containing, for example, water, ethanol, a polyol(e.g. glycerin, propylene glycol, liquid polyethylene glycol)suitable mixtures thereof and vegetable oils. The proper degree of fluidity can be maintained, for example by the use of a dispersant such as lecithin, by the maintenance of the required particle size and by the use of surfactants. The prevention of the action of microorganisms can be brought about by various antibacterial and antifungal agents, for example, parabens, chlorobutanol, phenol, sorbic acid, thimersol and the like. In many cases it will be preferable to include isotonic agents, for example, sugars or sodium chloride. Prolonged absorption of the injectable composition can be obtained by the use in the composition of agents which delay absorption, for example, aluminum monostearate and gelatin. Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile filtered solution thereof.

As used herein "pharmaceutically acceptable carrier" includes any and all solvents, dispersion media, coatings, antibacterial and antifungal agents, isotonic control agents, solid carriers and absorption control agents.

The oral administration of a compound of Formula 1 may be facilitated by the incorporation of a the selected compound in a tablet, pill, capsule or the like. The oral dosage form may also contain conventional excipients, binders, disintegrating agents, lubricants and or sweetening agents. Examples of excipients include dicalcium phosphate; binders include gum tragacanth, acacia, corn starch or gelatin; disintegrating agents include corn starch, potato starch or alginic acid; lubricants include magnesium stearate and the sweetening agents include sucrose, lactose and saccharin.

Various other materials may be present as coatings or as delayed release agents. A syrup or elixir may contain in addition to the active ingredient, a non caloric sweetening agent such as Aspartame or saccharin and a suitable liquid diluent which may be water or propylene glycol, preservatives, color and flavoring such as orange or cherry.

DESCRIPTION OF THE PREFERRED EMBODIMENT

The following description of the preferred embodiment is added to illustrate the practice of the invention and is not to be considered as limiting the scope of the invention.

EXAMPLE

Diabetes mellitus was induced in a group of male Sprague-Dawley rats (average weight 160 g.) by subcutaneous injection of 80 mg/Kg of body weight of streptozotocin (Sigma, Catolog No. S-0130).

The streptozotocin solution was prepared by dissolving 1.0 g of the streptazotocin in 25 ml of a solution of sodium citrate, pH 4.5 to give a concentration of 40 mg/ml of streptazotocin in the solution. Each rat except the control rats was given one injection of the streptozotocin after monitoring the condition of the rats for three days to assure that the rats were healthy.

Seven days after the administration of the streptozotocin and one day before sacrifice, the plasma glucose level was measured for each rat. Blood samples were obtained from the tail vein and not the retrobulbar sinuses in order to avoid interference with the study of protein glycation in the lenses of the eyes of the rats. The size of the blood sample did not in any case exceed 1% of the animals body weight. Plasma glucose concentrations of 400 mg/dl or higher were considered as a confirmation of the diabetic state. The weight of each animal was determined at least twice a week. One week before sacrifice, the eyes of each rats were examined by a veterinary ophthalmologist and the severity of cataracts was graded using a scale of 0 for no sign of a cataract and a grading system of 1 to 3 for assessing the severity of the cataract.

Eight groups of ten rats each were treated as follows:
A. Control group treated with water as placebo;
B. Untreated diabetic rats treated with distilled water as placebo;
C. Diabetic rats treated with 500 mg/Kg orally per day of L-arginine;
D. Diabetic rats treated with 624 mg/Kg orally per day of N-alpha-acetyl-L-arginine;
E. Diabetic rats treared with 100 mg/Kg orally per day of L-arginine;
F. Diabetic rats treated with 500 mg/Kg orally per day of L-Arginine;
G. Diabetic rats treated with 124 mg/Kg orally of N-alpha-acetyl L-arginine; and
H. Diabetic rats treated with 624 mg/Kg orally of N-alpha-acetyl L-arginine.

The dose of N-alpha-acetyl L-arginine was higher than the dose of L-arginine to provide an equimolar dose of each compound. Administration of the compounds was started 3 days prior to the induction of diabetes. The compounds were given in divided doses, twice a day dissolved in distilled water at a concentration that required less than 1 ml of liquid for each dose. The hydrochloride salt was used and the total weight of the dissolved salts was adjusted to provide that total amount of the amino acid portion at the stated dose. The pH of the arginine hydrochloride solution was about 5.5 and the pH of the distilled water that was administered as a control was also about 5.5 due to the dissolved atmospheric carbon dioxide.

After 98 days, all rats were sacrificed by carbon dioxide inhalation. Immediately after sacrifice, the skin, the tails, the eye lenses, aortic samples and the kidneys were dissected out of the animals.

The lens proteins were first extracted with phosphate buffer saline solution at pH 7.45, by homogenization, centrifugation and dialysis. The proteins in the supernatant were designated water soluble proteins. The resulting pellet was treated with 6M urea in phosphate buffered saline, pH 7.45, and centrifuged. The supernatant that was recovered was designated urea-soluble lens proteins.

The Maillard reaction products were measured by fluorescence in the near UV with a LKB Luminescence spectrometer, using an excitation wavelength of 340 nm and an emission wavelength of 420 nm. Prior to measurement, the water soluble proteins were digested with proteinase K to eliminate interference by light scattering and fluorescence quenching caused by the presence of intact cellular proteins.

Fluorescence was normalized to a constant value of protein concentration as determined by the Lowry method applied to the parent protein (before digestion) and correcting for dilution by K addition. The urea-soluble protein fluorescence was normalized on the basis of protein concentrations as measured with the Lowry method using urea-containing BSA standards. Fluorescence of urea insoluble proteins was normalized within respect to absorbance at 205 nm. This was based on the similarity of the absorption of both the peptide bond and the carboxyl group in the far UV.

Figure 2:
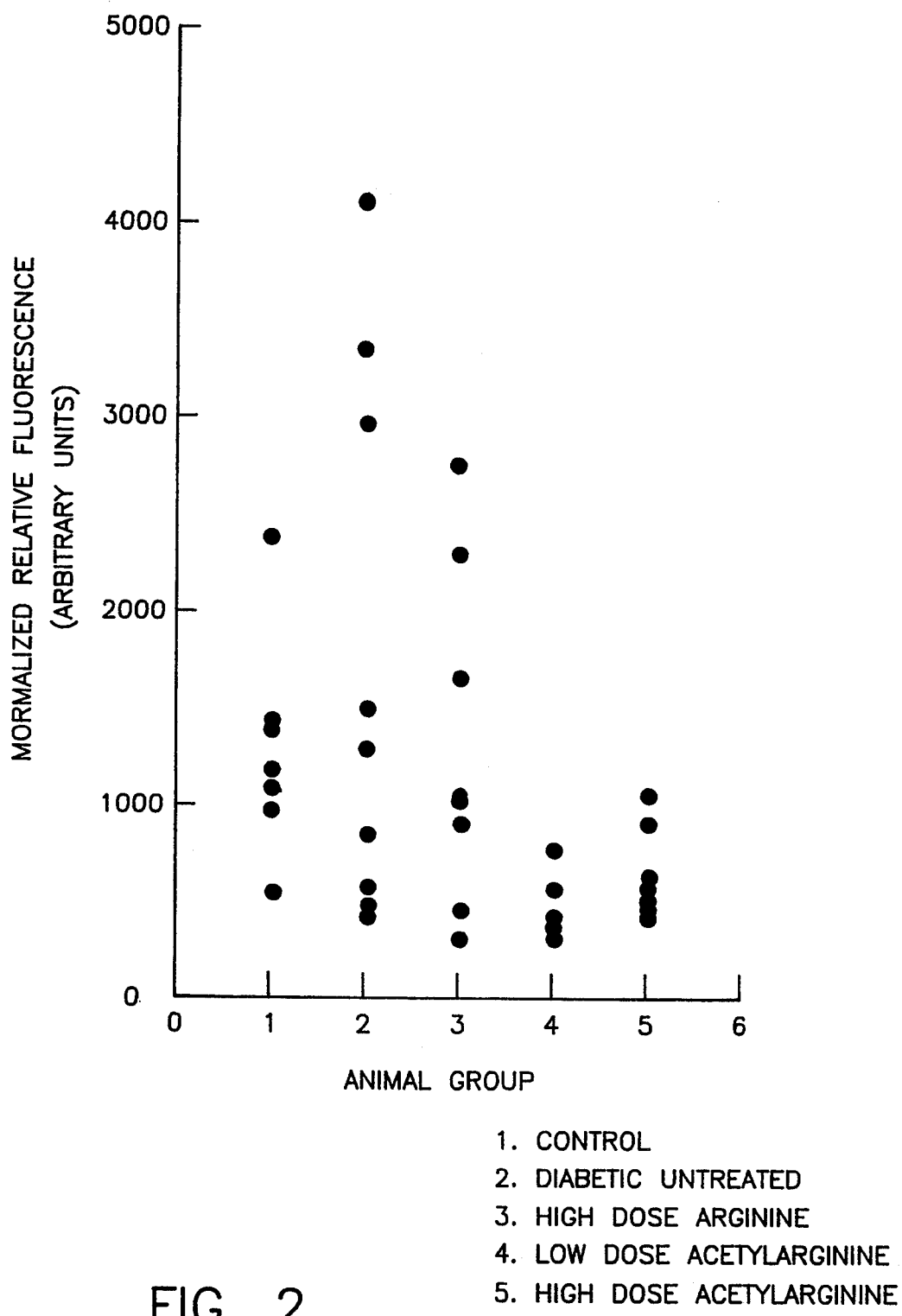
FIG. 2 is a graph which shows the effect of arginine and N-alpha acetyl arginine on the normalized protein fluorescence of water soluble lens proteins from diabetic rats.
Figure 3:
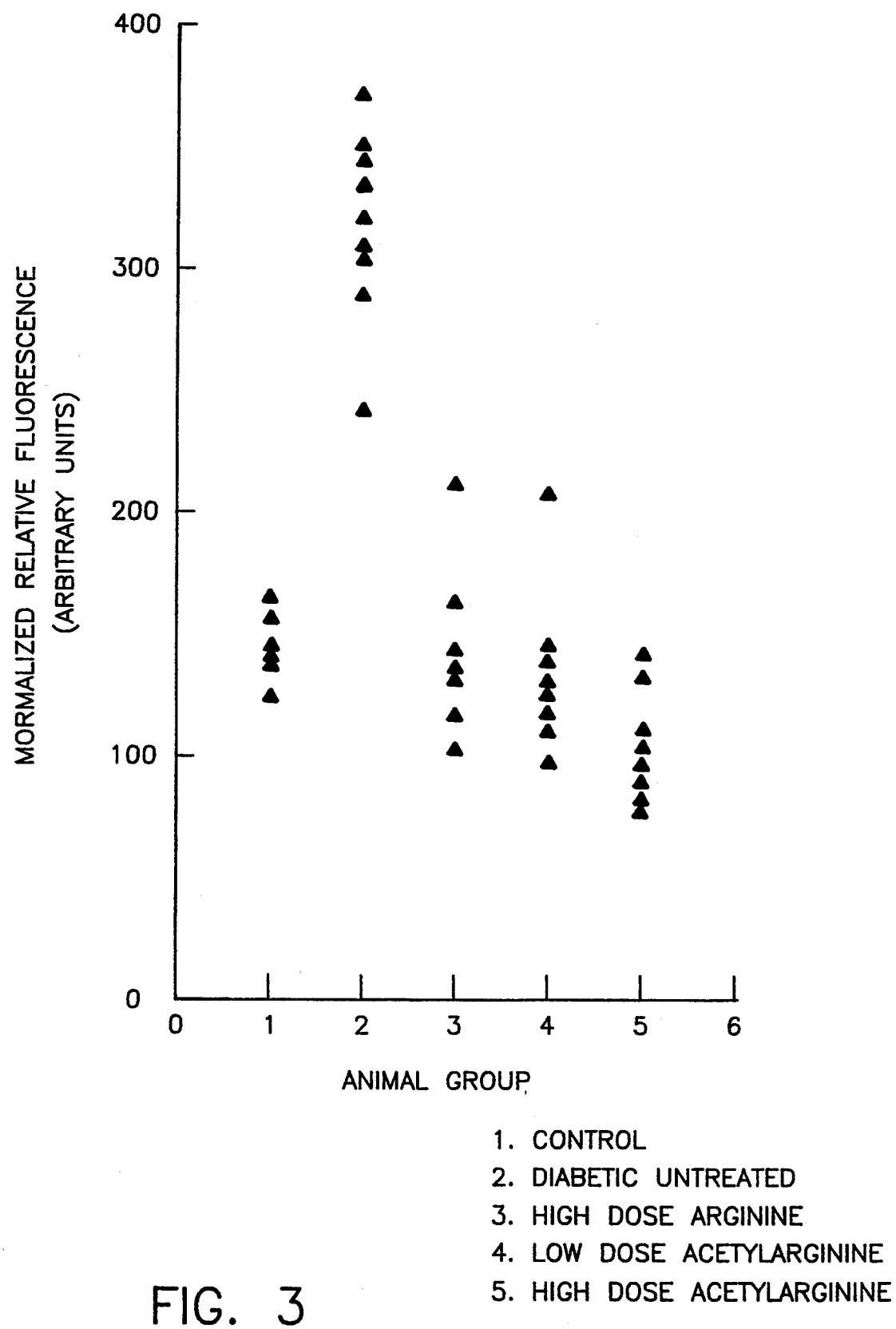
FIG. 3 is a graph which shows the effect of arginine and N-alpha acetyl arginine on the normalized protein fluorescence of urea soluble lens proteins from diabetic rats.

The test data in FIG. 1 show that the higher doses of arginine and N-alpha-acetyl arginine that were administered to the rats in Group F and Group G provided complete protection against cataracts in 20% of the test animals. This data from FIG. 1 has also been abstracted in Table I. FIG. 2 illustrates the highly significant decrease of the normalized protein fluorescence in the lens proteins of diabetic rats treated with N-alpha-acetyl L-arginine. The effect is even more remarkable in urea soluble lens proteins as illustrated in FIG. 3. Both arginine and N-alpha- acetyl L-arginine decreased the fluorescence, which shows more than a two fold increase in the untreated diabetic rats relative to the control animals. There was no demonstrable effect of arginine derivative treatment on the urea soluble lens proteins. However, diabetic animals did not show a unequivocal increase as compared to the control animals.

TABLE 1

|  | Glycemia mg/dl | Cataract Degree |
|---|---|---|
| Arginine 500 mg/Kg Animal | | |
| 1 | 220 | 0 |
| 2 | 480 | 0 |
| 3 | 490 | 1 |
| 4 | 570 | 1 |
| 5 | 460 | 2 |
| 6 | 470 | 2 |
| 7 | 500 | 2 |
| 8 | 510 | 2 |
| 9 | 510 | 3 |
| 10 | 525 | 3 |
| Acetylarginine 624 mg/Kg Animal | | |
| 1 | 160 | 0 |
| 2 | 240 | 1 |
| 3 | 420 | 1 |
| 4 | 460 | 1 |
| 5 | 500 | 2 |
| 6 | 520 | 2 |
| 7 | 370 | 3 |
| 8 | 420 | 3 |
| Acetylarginine 124 mg/Kg | | |
| 1 | 360 | 0 |
| 2 | 520 | 0 |
| 3 | 360 | 1 |
| 4 | 450 | 1 |
| 5 | 380 | 1 |
| 6 | 440 | 1 |
| 7 | 420 | 2 |
| 8 | 430 | 3 |
| 9 | 450 | 3 |
| 10 | 460 | 3 |

I claim:

1. A method for the palliation of the complications of diabetes mellitus, said method comprising administering to a host who is afflicted with diabetes mellitus an effective amount of N-alpha acetyl arginine.

2. A method as defined in claim 1 wherein the complication which is palliated is a cataract.

3. A method as defined in claim 1 wherein the effective amount is from about 50 mg/Kg to about 500 mg/Kg of body weight.

4. A method for the treatment of diabetes mellitus, said method comprising administering to a host who is afflicted with diabetes mellitus an effective amount of N-alpha acetyl arginine.

* * * * *

UNITED STATES PATENT AND TRADEMARK OFFICE
CERTIFICATE OF CORRECTION

PATENT NO. : 5,350,766
DATED : September 27, 1994
INVENTOR(S) : Gerardo Suarez

It is certified that error appears in the above-indentified patent and that said Letters Patent is hereby corrected as shown below:

On the title page, item [54] and column 1, line 4, change "ORGININE" to --ARGININE--.

Signed and Sealed this

Twenty-seventh Day of December, 1994

Attest:

BRUCE LEHMAN

*Attesting Officer*     *Commissioner of Patents and Trademarks*